(12) United States Patent
Stroppolo et al.

(10) Patent No.: US 8,440,170 B2
(45) Date of Patent: May 14, 2013

(54) ORALLY DISINTEGRATING TABLETS WITH SPECKLED APPEARANCE

(75) Inventors: Federico Stroppolo, Mezzovico (CH); Shahbaz Ardalan, Mezzovico (CH)

(73) Assignee: Alpex Pharma SA, Mezzovico (CH)

( * ) Notice: Subject to any disclaimer, the term of this patent is extended or adjusted under 35 U.S.C. 154(b) by 43 days.

(21) Appl. No.: 12/811,737

(22) PCT Filed: Jan. 30, 2009

(86) PCT No.: PCT/EP2009/051055
§ 371 (c)(1),
(2), (4) Date: Jul. 6, 2010

(87) PCT Pub. No.: WO2009/098169
PCT Pub. Date: Aug. 13, 2009

(65) Prior Publication Data
US 2010/0278754 A1    Nov. 4, 2010

Related U.S. Application Data

(60) Provisional application No. 61/026,249, filed on Feb. 5, 2008.

(51) Int. Cl.
*A61K 9/44* (2006.01)
*A61K 49/00* (2006.01)

(52) U.S. Cl.
USPC ................................... 424/10.2; 424/10.3

(58) Field of Classification Search ............... 424/10.2, 424/10.3
See application file for complete search history.

(56) References Cited

U.S. PATENT DOCUMENTS

| 3,555,144 A * | 1/1971 | Pazar et al. ............ 424/10.3 |
| 2003/0180357 A1* | 9/2003 | Martino et al. ............ 424/465 |
| 2004/0213855 A1* | 10/2004 | Pettersson et al. ........... 424/489 |

* cited by examiner

*Primary Examiner* — Fereydoun G Sajjadi
*Assistant Examiner* — Genevieve S Alley
(74) *Attorney, Agent, or Firm* — Rothwell, Figg, Ernst & Manbeck, P.C.

(57) ABSTRACT

Orally disintegrating tablets containing colored granules of a water-soluble sugar which give them a speckled appearance are described. The orally disintegrating tablets with speckled appearance are readily and easy identifiable by physicians, nurses and patients.

9 Claims, No Drawings

ORALLY DISINTEGRATING TABLETS WITH SPECKLED APPEARANCE

CROSS REFERENCE TO RELATED APPLICATION

This application is a 35 U.S.C. 371 National Phase Entry Application from PCT/EP2009/051055, filed Jan. 30, 2009, which claims the benefit of U.S. Provisional 61/026,249 filed Feb. 5, 2008, the disclosures of which are incorporated herein in their entirety by reference.

The present invention generally relates to the identification of orally disintegrating tablets. More particularly, the invention relates to orally disintegrating tablets with speckled appearance for their easy identification by physicians, nurses and patients.

Solid pharmaceutical dosage forms for oral administration are usually in pill, tablet or capsule form. These dosage forms are available in a limited variety of shapes, size, and colors, and many of them are very similar to each other in their outward appearance.

Frequently, users confuse such dosage forms, particularly if they are elderly or have limited vision. The consequences of taking the wrong medication can be life-threatening. For this reason Health Authorities require that each dosage form and strength must be clearly identified simply by individual visual inspection.

Identification of tablets is usually made by using different shapes, sizes, or colors, or by color coating, printing or embossing them. Very often a double identification is required such as embossing and coloring, or coating and printing, etc.

Also correct intake of drugs is important for their effectiveness.

Conventional tablets are swallowed, usually with some water or other liquids, and the absorption of the active ingredient occurs in the gastro-intestinal tract.

Orally Disintegrating Tablets (ODT) dissolve in the oral cavity by contact with saliva, do not require water for ingestion and could permit a buccal absorption of the active ingredient. The advantageous properties of ODT over conventional tablets are making them always more and more popular for drug administrations.

For their correct intake, it would be very helpful if ODT were more easily detectable and identifiable over conventional tablets.

In case of ODT physical identification methods are limited because ODT tablets are characterized by a low hardness which allows their rapid dissolution when in contact with saliva (i.e. EU pharmacopoeia requires a disintegration time of not more than 3 minutes in water).

Coating is not usually used because it could delay saliva penetration in the tablets, so delaying their disintegration.

As a consequence, identification of ODT by printing is also unusual because this technique requires a smooth and shining tablet surface, such as a film- or a sugar-coated tablet.

Embossing is possible but the dimension of characters is usually too small, due to the limited tablet surface, to be easily read by elderly people or by people with a limited vision.

Colored ODT can be prepared but the limited number of pharmaceutically acceptable colors make difficult to obtain an ODT easily identifiable over conventional colored tablets.

One way to solve the problem would be to make ODT identifiable by using a particular colored pattern.

ODT with speckled (spotted) appearance, i.e. with a bicolored appearance characterized by the presence of spots of a different color on their surface can be easily identified by users. For example, blue spots on a white or yellow tablet surface are easily visible, making such tablets more identifiable than white or monocolored tablets.

Solid or semisolid forms with speckled appearance are very common among cosmetic and laundry products, such as tooth pastes or soaps.

They are prepared by incorporating colored beads of a different material into the composition.

In case of ODT, the colored beads must be soluble and dissolve as fast as the tablets to avoid an unpleasant grinding sensation when the tablet disintegrates in the oral cavity. Moreover, the colored beads must be stable, i.e. they must not release the color during storage, and should give minimal coloration of the oral cavity after disintegration of the tablet.

The present invention relates to orally disintegrating tablets containing colored granules which give a speckled appearance to the tablets for their readily and easy identification by physicians, nurses and patients.

The orally disintegrating tablets of the invention contains colored granules of a water-soluble sugar.

The present invention relates to orally disintegrating tablets (ODT) with speckled appearance which make them readily identifiable by users.

The ODT with speckled appearance are prepared by mixing soluble colored granules to the pharmaceutically acceptable carrier.

The term "colored granules" as used herein after means granules of a color different from the color of the tablet. Colored granules are, for example, blue or yellow granules in a white tablet, blue or white granules in a yellow tablet, yellow or white granules in a blue tablet, dark blue granules in a light blue tablet, blue granules and red granules in a white tablet, etc.

The soluble colored granules are granular particles of a water-soluble sugar such as sucrose or a polyalcohol. Specific examples of polyalcohols are sorbitol, mannitol, xylitol, fructose, etc.

Preferably, the same polyalcohol already present in the pharmaceutically acceptable carrier of the ODT is used for the preparation of the colored granules of the invention.

Preferably, the ODT of the present invention contains colored granules of mannitol.

Even if water-soluble sugars are excipients usually present in ODT, their use to prepare colored granules suitable for the preparation of ODT with speckled appearance requires a specific particle size.

In fact, the particle size of the colored granules is critical. Colored granules with too small particle size are not visible and the resulting tablets have no speckled appearance. On the other side, the use of colored granules with too large particle size results in a tablet which appears uniformly colored and therefore not readily identifiable over mono-colored tablets.

The colored granules used in the ODT of the present invention have a particle size from about 10 μm to about 1200 μm, preferably from about 200 μm to about 800 μm, most preferably from about 300 μm to about 500 μm.

The selection of the particle size of the colored granules of the ODT of the present invention depends on several factors. Since the sucrose or polyalcohol used for the colored granules is preferably one of the excipients already present in the ODT, the particle size must be different from the particle size of the already present excipient.

The selection of the suitable particle size also depends on the desired colored pattern. For example, the use of a little quantity of large particles tends to produce an ODT with few large colored spots on its surface. Higher amount of smaller particles tends to produce less discrete colored spots on the surface of the tablets.

Then, the amount of colored granules suitable for each tablet, according to the present invention, can vary within a relatively large range depending on the particle size of the granule. Preferably, the amount of colored granules ranges between about 0.1% w/w and about 50% w/w, still more preferably between about 1% w/w and about 30% w/w.

Preferably the colored granules useful for the ODT with speckled appearance of the present invention are prepared by granulation of the water-soluble sugar with an aqueous suspension or solution of the coloring agent in a suitable fluid bed granulator.

Any soluble or insoluble pharmaceutically acceptable coloring agent can be used.

Non limiting examples of suitable coloring agents are FD&C blue no. 1 aluminum lake, FD&C blue no. 2 aluminum lake, FD&C green no. 1 aluminum lake, FD&C green no. 3 aluminum lake, FD&C red no. 2 aluminum lake, FD&C red no. 3 aluminum lake, FD&C red no. 6 aluminum lake, FD&C red no. 7 aluminum lake, FD&C red no. 21 aluminum lake, FD&C red no. 27 aluminum lake, FD&C red no. 28 aluminum lake, FD&C red no. 30 aluminum lake, FD&C red no. 33 aluminum lake, FD&C red no. 40 aluminum lake, FD&C yellow no. 5 aluminum lake, FD&C yellow no. 6 aluminum lake, FD&C yellow no. 10 aluminum lake, ferric oxide yellow, ferric oxide brown, ferric oxide red, and mixture thereof.

The colored granules are incorporated into the composition of the ODT by conventional blending procedures. The ODT according to the present invention are then prepared by compression of the resulting mixture containing the colored granules.

Since the incorporation of the colored granules does not change the manufacturing process and the characteristics of the ODT, the ODT with speckled appearance according to the present invention may be of any shape known among conventional ODT, may be embossed on the surface with symbol(s), letter(s) and/or number(s), may be scored, etc.

The ODT with speckled appearance according to the present invention have the same disintegrating properties of ODT of reference (i.e. without colored granules). Moreover, a the coloring agent does not spread over the tablet and the colored pattern is stable over time.

The ODT with speckled appearance of the present invention can be a placebo tablet or preferably contain one or more active ingredients.

Non-limiting examples active ingredients which can be present in the ODT according to the present invention are: abortifacients such as prostaglandin $E_2$, and mifepristone; ACE inhibitors such as benazepril, captopril, delapril, enalapril, imidapril, and ramipril; α-adrenergic agonists such as adrenolone, clonidine, ephedrine, epinephrine, fenoxazoline, ibopamine, methoxamine, nafazoline phenylephrine, phenylpropanolamine, pseudoephedrine, tetrahydrozoline, tramazoline, tuaminoheptane, and tyramine xylomethazoline; β-adrenergic agonists such as albuterol, bambuterol, clenbuterol, clorprenaline, dopexamine, ephedrine, epinephrine, ethylnorepinephrine, fenoterol, formoterol, isoproterenol, mabuterol, metaproterenol, methoxyphenamine, oxyfedrine, reproterol, salmeterol, soterenol, terbutaline, tulobuterol, and xanoterol; α-adrenergic blockers such as dapiprazole, fenspiride, nicergoline, prazosin, and yohimbine; β-adrenergic blockers such as acebutolol, alprenolol, atenolol, befnolol, betaxolol, bupranolol, carazolol, carteolol, celiprolol, indenolol, levobunolol, mepindolol, metipranolol, moprolol, pindolol, practolol, propranolol, and timolol; adrenocortical steroid; adrenocorticotropic hormones such as ACTH cosintropin; alcohol deterrents such as calcium cianamide citrate, and disulfiram; aldose reductase inhibitors such as epalrestat, tolrestat, and zopolrestat; aldosterone antagonists such as canrenone, and spironolattone; anabolics such as androisoxazole, androstenediol, methandriol, methenolon, methyltrienolone, and nandrolone; narcotic analgesics such as alfentanil, buprenorphine, codeine and its derivatives, fentanil, meperidine, methadone, morphine and its derivatives, pentazocine, phenazocine, propiram, propoxiphene, and sufentanil; non narcotic analgesics such as aceclofenac, acetaminophen, acetylsalicylic acid, alclofenac, alminoprofen, antypirine, benorilate, benoxoprofen, bromfenac, bucetin, carbamazepine, carbiphene, chlortenoxazin, cholin salicylate, clometacin, clonixin, chloropamide, diflunisal, etodolac, felbinac, fenoprofen, flufenamic acid, flurbiprofen, ibufenac, imidazole salicylate, indomethacin, indoprofen, ketoprofen, ketorolac, mofezolac, naproxen, nifenazone, phenacetin, propyphenazone, sutrofen, tenoxicam, terofenamate, tolfenamic acid, tramadol, and viminol; androgens such as boldenone, cloxotestosterone, mestanolone, mesterolone, methandrostenolone, norethandrolone, normethandrone, oxandrolone, oxymesterone, oxymetholone, prasterone, stanolone, stanozolol, and testosterone; angiotensin II receptor antagonists, such as candesartan, eprosartan, ibesartan, losartan, and valsartan; anorexic agents such as a minorex, amphecloral, anphetamine, benzphetamine, chlorphentermine, clobenzorex, clortermine, fenfluramine, norpseudoephedrine, pentorex, phendimetrazine, phenmetrazine, and phentermine; anthelmintic agents such as arecoline, aspidin, aspidinol, becanthone, and hycantone; antiallergic agents such as amlexanox, astemizole, azelastine, cromolyn, fempiprane, ibudilast, lodoxamide, nedocromil, oxatomide, repirinast, tazanolast, hystamine, beclomethasone, dexamethasone, flunisolide, fluticasone, and triamcinolone; antialopecia agents such as cioteronel, and minoxidil; antiamebic agents such as arsthinol, carbasone, chlorbetamide, chloroquine, chlorphenoxamide, emetine, fumaggilline, and iodoquinol; antiarrhythmic agents such as acebutol, adenosine, ajmaline, alprenolol, amiodarone, atenolol, bupranolol, carazolol, carteolol, cloranolol, indenolol, ipratropium bromide, lidocaine, pindolol, propafenone, propranolol, quinidine, timolol, and verapamil; antiarteriosclerotic agents such as pyridinol carbamate; antiarthritic/antirheumatic agents such as actarit, auranofin, aurothioglucose, aurothioglicanide, azathioprine, chloroquine, gold sodium thiosulfate, hydroxchloroquine, and methotrexate; antiasmatic agents such as azelastine, cromolyn, ibudilast, ketotifen, montelukast, oxotomide, pranlukast, seratrodast, zafirlukast, zileuton, beclomethasone, budesonide, dexamethasone, flunisolide, and triamcinolone acetonide; antibacterial agents such as amikacin, gentamicin, kanamycin, neomicin, tobramycin, chloramphenicol, thiamphenicol, rifamide, rifampin, rifamycin, rifapentine, rifaximin, cefaclor, cefamandole cefazolin, cefitime, cefoxitin, amoxicillin, ampicillin, oxacillin, lindomycin, erytromycin, gramicidin, teicoplanin, vancomycin, chlortetracyclin, doxycylline, tetracyclin, trimetoprim, nifuradene, nitrofurantoin, ciprofloxacin, ofloxacin, lomefloxacin, benzylsulfamide, chloramine-t, mafenide, sulfabenzamide, sulfacetamide, sulfadiazine, sulfadoxine, sulfaguanidine, sulfalene, sulfanilamide, sulfanylurea, sulfatyazole, sulfisoxazole, acedapsone, dapsone, solasulfone, ethinamide, furonazide, isoniazide, and streptomicyn; anticholinergic agents such as atropine, fentonium bromide, homatropine, hyoscyamine, ipratropium bromide, isopropramide iodide, scopolamine, and tropicamide; anticoagulant agents such as acecumarol, bromindione, clorindione, coumetarol, dicumarol, diphenadione, fluindione, heparin, hirudin, pheninedione, and warfarin; anticonvulsant agents such as albutoin, aloxidone, aminoglutethimide, beclamide, carbamazepine, clonazepam, ethadine, ethotoin, felbamate, mephenytoin, narcobarbital, nimethazepam, nitrazepam, paramethadione, phenacemide, phenobarbital, and phenitoin; antidepressant agents such as citalopram, fencaine, nefopam, iproclozide, isocarboxazid, nialamide, rolyciprine, maprotiline, metralindole, amytriptiline, clomipramide, desipramide, dibenzepin, imipramide, trimipramide, and bupropion; antidiabetic agents such as buformin, phenformin, insulin, carbutamide, chlorpopamide, glipizide, phenbutamide, tolazamide, tolbutamide, and tolcyclamide; antidiarreal agents such as acetorphan, catechin, difenoxin, diphenoxylate, loperamide, and mebiquine; antidiuretic agents such as desmopressin, felypressin, ornipressin, and vasopressin; antidotes such as acetylcysteine, cysteamine, methionine, and folinic acid; antidyskinetic agents such as amantidine, clonidine, haloperidol, pimozide, and tetrabenazine; antiemetics such as alizapride, azasentron, benzquinamide, bromopride, buclizine, chlorpromazine, cyclizine, domperidone, granisetron, meclizine, metoclopramide, ondansentron, prochlorerazine, scopolamine, sulpiride, and tropistron; antifungal agents such as butenafine, butoconazole, econazole, fenticonazole, miconazole, tolciclate, tolindate, fluconazole, buclosamide, and triacetin; antiglaucoma agents such as acetozolamide, betaxolol, and bupranolol; antigout agents such as allopurinol, colchicine, probenecid, and sulfipyrazone; anthistaminic agents such as acrivastine, brompheniramine, chlorpheniramine, dimethindene, pheniramine, tolpropamine, clemastine, diphenidramine, medrilamyne, cetirizine, chlorcyclizine, cinnarizine, hidroxyzine, fenethazine, promethazine, loratadine, antazoline, astemizole, azelastine, ebastine, fexofenadine, and terfenadine; antihyperlipoproteinemic agents such as cholestiramine, benzofibrate, clofibrate, etofibrate, genfibrozil, atorvastatin, lovastatin, niceritrol, thyroxine, carnitine, chondroitinsulfate, ornithine, and probucol; antihypertensive agents such as bufuralol, acebutolol, atenolol, carteolol, metoprolol, moprolol, pindolol, propranolol, timolol, chlorthiazide, cyclopenthiazide, hydroflumethazide, benazepril, captopril, lisinopril, ramipril, amlodipine, felodipine, lacidipine, nicardipine, nitrendipine, bethnide, budralazine, hydralazine; pheniprazine, phentolamine, bunazosin, prazosin, reserpine, furosemide, ajmaline, fenoldopam, mebutamate, methildopa, and minoxidil; antihypotensive agents such as dopamine, etilefrin, norepinephrine, and synephrine; nonsteroidal antiinflammatory agents such as etofenamate, flufenamic acid, mecoflenamic acid, tolfenamic acid, aceclofenac, alclofenac, bromfenac, diclofenac sodium, etodolac, ibufenac, indomethacin, pirazolac, sulindac, tolmetin, fenbufen, ketorolac, alminoprofen, fenoprofen, flurbiprofen, ibuprofen, ketoprofen, naproxen, feprazone, benorylate, piroxicam, bendazac, and nimesulide; antimalaria agents such as chloroquine, chlorproquanil, cinchonide, cycloguanil, and quinidine; antimigraine agents such as dolasetron, ergocornine, ergocriptyne, ergot, ergotamine, lomerizine, and sumatriptan; antiparkinson agents amantadine, bromocriptine, carbidopa, and levodopa; antipsychotic agents alizapride, amilsulpiride, sulpiride, risperidone, haloperidol, acetophenazine, chlorpromazine, fluphenazine, and perazine; antipyretic agents such as acetaminophen, alclofenac, aspirin, benorilate, and indomethacin; antispasmodic agents aminopromazine, fentonium bromide, rociverine, and tiropramide; antitussives such as cloperastine, codeine and derivatives, dextromethorphan, and morclofone; antiulcerative agents acetoxolone, cimetidine, famotidine, omeprazole, pirenzepine, ranitidine, and sucralfate; anxiolytic agents such as buspirone, alprazolam, bromazepam, camazepam, lorazepam, nordazepam, and meprobamate; bronchodilators such as albuterol, bambuterol, calbiterol, clenbuterol, clorprenaline, ephedrine, ephineprine, folmoterol, metaproterenol, salmeterol, terbutaline, ipratroprium bromide, and teophilline and derivatives; calcium channel blockers such as diltiazem, verapamil, amlodipine, lacidipine, micardipine, nifedipine, and nomerizine; cardiotonic agents such as digitalin, digitoxin, digoxin, dopamine, uabain, and scillaren; choleretic agents such as cholic acid, cynerin, dehydrocholic acid, dehoxycolic acid, and taurocolic acid; cholinergic agents such as acetylcholine, benzepirinium bromide, carbachol, neostigmine, and physostigmine; CNS stimulants such as amphetamine, caffeine, fenozolone, and phentermine; diuretic agents such as bendroflumethiazide, benzylhytrochlorothiazide, chlorothiazide, indapamide, mersalil, candrenone, oleandrin, spironolattone, acetazolamide, butazolamide, clopramide, furosemide, and isosorbide; dopamine receptor agonists such as bromocriptine, cabercoline, dopexamine, and fenoldopam; dopamine receptor antagonists such as amisulpride, domperidone, metoclopamide, and sulpiride; enzymes such as amylase, lysozyme, and papain; expetorants such as ambroxol, bromhexine, carbocysteine, guaiacol, and guaifenesin; gastric and pancreatic secretion stimulants such as carnitine, and ceruletide; gastric proton pump inhibitors such as lansoprazole, omeprazole, and pantoprazole; gastric secretion inhibitors such as enterogastrone, octretide, and telenzepine; gastroprokinetic agents such as cinitapride, cisapride, fenotozine, and loxiglumide; glucocorticoids such as beclomethasone, bethometasone, budesonide, chloroprednisone, clobetasone, cortisone, corticosterone, deflazacort, dexamethasone, fluazacort, flumethasone, flunisolide, fluocinolone acetonide, fluorometholone, fluprednisolone, hydrocortisone, methylprednisolone, prednisolone, prednisone, and triamcinolone; hemolytic agents such as phenilhydrazine; histamine $H_2$-receptor antagonists such as cimetidine, ebrotidine, famotidine, nizatidine, and ranitidine; laxative/cathartic agents such as frangulin, phenolphtaleine, and picosulfate sodium; leukotriene antagonists such as ibudilast, montelukast, pranlukast, and zafirlukast; lipotropic agents such as buserelin, goserelin, histrelin, leuprolide, nafarelin, and triptorelin; mineralcorticoid agents such as aldosterone, deoxycorticosterone, and fludrocortisones; monoamine oxidase inhibitors such as iproniazid, moclobemide, phenoxypropazine, and selegeline; mucolitic agents such as acetylcysteine, bromexine, carbocysteine, lysozime, sobrerol, and tyloxapol; muscle relaxants such as afloqualone, baclofen, curare, cyclarbamate, dandrolene, decamethonium bromide, diazepam, eperisone, flumetramide, mephenesin, mephenaxolone, methaxolone, methocarbamol, nimethazepam, succiynylcholine bromide, tetrazepam, and tubocurarine; narcotic antagonists such as amiphenazole, naloxone, and naltaxone; nootropic agents such as aceglutamide, besipiride, piracetam, and vinconate; oxytocic agents such as carboprost, deaminooxytocic, ergonovine, gemeprost, methylergonovine, oxytocin, prostaglandin $E_2$, and prostaglandin $F_{2a}$; progestogens such as drospirenone, dydrogesterone, ethynodiol, flurogestone acetato, lynestrenol, medrogestone, medroxyprogesterone, megestrol acetate, norgesterone, pentagestrone, and progesterone; prolactin inhibitors such as bromocriptine, cabergoline, lisuride, metergoline, and quinagoline; prostaglandins and analogs such as beraprost, carboprost, enprostil, gemeprost, limaprost, misoprostol, prostacyclin, and prostaglandin $E_1, E_2, F_{2a}$; respiratory stimulants such as almitrine, bemegride, cropropamide, dimorpholamine, lobeline, and pyridopylline; retroviral transcriptase inhibitors such as delavirdine, didanosine, dideoxyadenosine, lamivudine, stavudine, and zidovudine; sedative/hypnotics such as acecarbromal, butoctamide, diethylbromoactamide, niaprazine, trimetozine, zolpidem, zopiclone, allobarbital, amobarbital, barbital, cyclopentobarbital, hexobarbital, mephobarbital, narcobarbital, pentobarbital, phenobarbital, tetrabarbital, estazolam, flunitrazepam, flurazepam, loprazolam, lormetazepam, nitrazepam, piperidione, acetophenone, clomethiazole, doxylamine, temazepam, triazolam, methaqualone, and glutethimide; serotonin/noradrenaline reuptake inhibitors such as duloxetine, and venlafaxine; serotonin reuptake agonists such as buspirone, eltoprazine, ergotamine, and sumatriptan; serotonin receptor antagonists such as azasentron, dolasentron, granisentron, ondasentron, ritanserin, and tropisentron; serotonin uptake inhibitors such as fomexitine, fluoxetine, and paroxetine; vasodilators such as cinnarizine, citicoline, fenoxedil, flunarizine, lomerizine, nicergoline, nimodipine, papaverine, vincamine, amotriphene, efloxate, nitroglicerin, pentrinitrol, trapidil, bradykinin, inositol, nicergoline, pentifillyne, and tolazoline; vitamins such as calcitriol, ergosterol, vitamin A, B and related B complex, D and D complex, E, K, ascorbic acid, β-carotene, and pantothenic acid; minerals such as calcium salts, phosphorous salts, iodine salts, iron salts, magnesium salts, potassium salts, chloride salts, chromium salts, molybdenum salts, silicon and its salts, manganese salts, zinc salts, selenium salts, boron salts, nickel salts, tin salts, and vanadium salts.

The ODT with speckled appearance of the present invention can be prepared by incorporation of the soluble colored granules into any conventional ODT preparable by compression. Non-limiting examples of these conventional ODT are those disclosed in U.S. Pat. No. 6,149,938 (Elan), U.S. Pat. No. 6,024,981 (Cima), U.S. Pat. No. 6,221,392 (Cima), U.S. Pat. No. 5,215,756 (Janssen), U.S. Pat. No. 5,264,632 (Prographarm) and U.S. Pat. No. 6,872,405 (Yamanouchi).

Preferably the ODT with speckled appearance of the present invention are prepared by using the method described in U.S. Pat. No. 6,149,938.

In a preferred practical embodiment, the manufacturing process of the ODT with speckled appearance object of the present invention is the following.

The active ingredient and the excipients are granulated in a suitable fluid bed granulator. The colored granules and optional further excipients are added to the external phase and the resultant mixture is blended in a suitable mixer. The blended mixture is then compressed in a tabletting machine with punches of the desired shape obtaining ODT with speckled appearance according to the present invention.

The following examples better illustrate the present invention without limiting it.

EXAMPLE 1

Preparation of Blue Granules

Perlitol® 400 (500 g) was placed in a fluid bed granulator Strea 1.

A homogeneous suspension of FD&C blue no. 1 (1 g) in purified water (50 ml) was prepared.

Air at about 30° C. was blown in the fluid bed and the suspension was sprayed on the granular.

At the end of spraying, the granular was dried at 40° C. until a residual moisture of not more than (NMT) 0.5%.

The obtained granular was intensively colored in blue.

EXAMPLE 2

Example 2A

Perlitol® 160C (447.5 g), sucralose (5.5 g), citric acid (40 g), Povidone CL (Kollidon® CL—30.00 g) and Povidone K 30 (Kollidon® 30—6 g) were placed in a fluid bed granulator Strea 1.

Separately a quantity of purified water (50 ml) was prepared. This solution was sprayed on the granular. At the end of spraying, the granular was dried at 40° C. until a residual moisture of NMT 0.5%.

The resultant granular was mixed in a cube blender mix with peppermint flavor (5 g), magnesium stearate (6.00 g) and the colored granular (60 g) prepared as described in the example 1.

The mixture was blended until homogeneity and compressed in round biconcave tablets weighing 600 mg each.

Example 2B

Perlitol® 160C (507.5 g), sucralose (5.5 g), citric acid (40 g), Povidone CL (Kollidon® CL—30.00 g) and Povidone K 30 (Kollidon® 30—6 g) were placed in a fluid bed granulator Strea 1.

Separately a quantity of purified water (50 ml) was prepared. This solution was sprayed on the granular. At the end of spraying, the granular was dried at 40° C. until a residual moisture of NMT 0.5%.

The resultant granular was mixed in a cube blender mix with peppermint flavor (5 g) and magnesium stearate (6.00 g).

The mixture was blended until homogeneity and compressed in round biconcave tablets weighing 600 mg each.

The comparison between the physical characteristics of the tablets prepared according to example 2A and according to example 2B is reported in the following table 1.

TABLE 1

Comparison between the physical characteristics of the tablets of examples 2A and 2B

| | Tablets of example 2A | Tablets of example 2B |
|---|---|---|
| Appearance | White tablets with blue speckles | White homogeneous tablets |
| Diameter | 14 mm | 14 mm |
| Thickness | 4.4 mm | 4.4 mm |
| Friability | NMT 1% | NMT 1% |
| Disintegration time in vitro (USP basket apparatus for tablets disintegration) | NMT 60 seconds | NMT 60 seconds |
| Disintegration time in vivo (mean of 3 healthy volunteers) | 45 seconds | 45 seconds |
| Grinding sensation in the mouth during disintegration of tablets | Absent | Absent |

The above data clearly shows that the presence of colored granules confers a easy identifiable colored pattern to the ODT and does not affect the other physical characteristics of the ODT, in particular the disintegration characteristics.

EXAMPLE 3

Phentermine hydrochloride (37.5 g), Perlitol® 160C (410 g), sucralose (5.5 g), citric acid (40 g), Povidone CL (Kollidon® CL—30.00 g) and Povidone K 30 (Kollidon® 30—6 g) were placed in a fluid bed granulator Strea 1.

Separately a quantity of purified water (50 ml) was prepared. This solution was sprayed on the granular. At the end of spraying, the granular was dried at 40° C. until a residual moisture of NMT 0.5%.

The resultant granular was mixed in a cube blender mix with peppermint flavor (5 g), magnesium stearate (6.00 g) and the colored granular (60 g) prepared as described in the example 1.

The mixture was blended until homogeneity and compressed in round biconcave tablets weighing 600 mg each and containing 37.5 mg of phentermine hydrochloride.

The physical characteristics of the resulting ODT are reported in the following table 2.

TABLE 2

| | |
|---|---|
| Appearance | White scored tablets with blue speckles and embossed with AX2 |
| Diameter | 14 mm |
| Thickness | 4.4 mm |
| Friability | NMT 1% |
| Disintegration time in vitro (USP basket apparatus for tablets disintegration) | NMT 60 seconds |
| Disintegration time in vivo (mean of 3 healthy volunteers) | 45 seconds |
| Grinding sensation in the mouth during disintegration of tablets | Absent |

EXAMPLE 4

Phentermine hydrochloride (30 g), Perlitol® 160C (356.3 g), sucralose (5.5 g), citric acid (40 g), Povidone CL (Kollidon® CL—30.00 g) and Povidone K 30 (Kollidon® 30—6 g) were placed in a fluid bed granulator Strea 1.

Separately a solution of purified water (50 ml) containing FD&C yellow lake no. 5 (1.2 g) was prepared. This solution was sprayed on the granular. At the end of spraying, the granular was dried at 40° C. until a residual moisture of NMT 0.5%.

The resultant yellow granular was mixed in a cube blender mix with peppermint flavor (5 g), magnesium stearate (6.00 g) and Perlitol® 400 DC (120 g).

The mixture was blended until homogeneity and compressed in round biconcave tablets weighing 600 mg each and containing 30 mg of phentermine hydrochloride.

The physical characteristics of the resulting ODT are reported in the following table 3.

TABLE 3

| | |
|---|---|
| Appearance | Yellow tablets with white speckles and embossed with AX3 |
| Diameter | 14 mm |
| Thickness | 4.4 mm |
| Friability | NMT 1% |
| Disintegration time in vitro (USP basket apparatus for tablets disintegration) | NMT 60 seconds |
| Disintegration time in vivo (mean of 3 healthy volunteers) | 45 seconds |
| Grinding sensation in the mouth during disintegration of tablets | Absent |

EXAMPLE 5

Phentermine hydrochloride (15 g), Perlitol® 160C (178.15 g), sucralose (2.75 g), citric acid (20 g), Povidone CL (Kollidon® CL—15.00 g) and Povidone K 30 (Kollidon® 30—3 g) were placed in a fluid bed granulator Strea 1.

Separately a solution of purified water (25 ml) containing FD&C yellow lake no. 5 (0.6 g) was prepared. This solution was sprayed on the granular. At the end of spraying, the granular was dried at 40° C. until a residual moisture of NMT 0.5%.

The resultant yellow granular was mixed in a cube blender mix with peppermint flavor (2.5 g), magnesium stearate (3.00 g) and the colored granular (60 g) prepared as described in the example 1.

The mixture was blended until homogeneity and compressed in round tablets weighing 300 mg each and containing 15 mg of phentermine hydrochloride.

The physical characteristics of the resulting ODT are reported in the following table 4.

TABLE 4

| | |
|---|---|
| Appearance | Yellow tablets with blue speckles, embossed with AX4 |
| Diameter | 10 mm |
| Thickness | 3.4 mm |
| Friability | NMT 1% |
| Disintegration time in vitro (USP basket apparatus for tablets disintegration) | NMT 60 seconds |
| Disintegration time in vivo (mean of 3 healthy volunteers) | 30 seconds |
| Grinding sensation in the mouth during disintegration of tablets | Absent |

EXAMPLE 6

Meloxicam (15 g), Perlitol® 160C (432.5 g), sucralose (5.5 g), citric acid (40 g), Povidone CL (Kollidon® CL—30.00 g) and Povidone K 30 (Kollidon® 30—6 g) were placed in a fluid bed granulator Strea 1.

Separately a quantity of purified water (50 ml) was prepared. This solution was sprayed on the granular. At the end of spraying, the granular was dried at 40° C. until a residual moisture of NMT 0.5%.

The resultant granular was mixed in a cube blender mix with strawberry flavor (5 g), magnesium stearate (6.00 g) and the colored granular (60 g) prepared as described in the example 1.

The mixture was blended until homogeneity and compressed in round biconcave tablets weighing 600 mg each and containing 15 mg of meloxicam.

The physical characteristics of the resulting ODT are reported in the following table 5.

TABLE 5

| | |
|---|---|
| Appearance | White tablets with blue speckles |
| Diameter | 14 mm |
| Thickness | 4.4 mm |
| Friability | NMT 1% |
| Meloxicam content | 15 mg |
| Disintegration time in vitro (USP basket apparatus for tablets disintegration) | NMT 60 seconds |
| Disintegration time in vivo (mean of 3 healthy volunteers) | 40 seconds |
| Grinding sensation in the mouth during disintegration of tablets | Absent |

The invention claimed is:

1. An orally disintegrating tablets with speckled appearance comprising (a) speckles comprising colored granules of a water-soluble sugar, and (b) a pharmaceutically acceptable carrier.

2. The orally disintegrating tablets according to claim 1 wherein the water-soluble sugar is selected from the group consisting of sucrose and polyalcohols.

3. The orally disintegrating tablets according to claim 2 wherein the water-soluble sugar is selected from the group consisting of sucrose, sorbitol, mannitol, xylitol, and fructose.

4. The orally disintegrating tablets according to claim 3 wherein the water-soluble sugar is mannitol.

5. The orally disintegrating tablets according to claim 1 wherein the colored granules have a particle size from about 10 μm to about 1200 μm.

6. The orally disintegrating tablets according to claim 5 wherein the colored granules have a particle size from about 200 μm to about 800 μm.

7. The orally disintegrating tablets according to claim 6 wherein the colored granules have a particle size from about 300 μm to about 500 μm.

8. The orally disintegrating tablets according to claim 1 wherein the colored granules are present in an amount from about 0.1% w/w to about 50% w/w per tablet.

9. The orally disintegrating tablets according to claim 1 wherein the colored granules are present in an amount from about 1% w/w to about 30% w/w.

* * * * *